United States Patent
Dick et al.

(10) Patent No.: US 7,591,836 B2
(45) Date of Patent: Sep. 22, 2009

(54) SURGICAL DEVICES AND METHODS FOR VERTEBRAL SHIFTING UTILIZING SPINAL FIXATION SYSTEMS

(75) Inventors: Jeffrey Clayton Dick, Wayzata, MN (US); Michael J. McNamara, Nashville, TN (US); Paul F. Boschert, Minneapolis, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 687 days.

(21) Appl. No.: 10/903,910

(22) Filed: Jul. 30, 2004

(65) Prior Publication Data
US 2006/0025769 A1  Feb. 2, 2006

(51) Int. Cl.
*A61B 17/70* (2006.01)

(52) U.S. Cl. .................. 606/246; 606/264; 606/265; 606/279

(58) Field of Classification Search .................. 606/61, 606/86, 90, 246–279, 86 A, 86 R; 81/10, 81/13, 44, 437, 459
See application file for complete search history.

(56) References Cited

U.S. PATENT DOCUMENTS

| | | | | |
|---|---|---|---|---|
| 1,334,261 A | * | 3/1920 | Robus et al. | 81/124.2 |
| 4,611,581 A | * | 9/1986 | Steffee | 606/61 |
| 4,716,894 A | * | 1/1988 | Lazzeri et al. | 606/91 |
| 5,219,349 A | | 6/1993 | Krag et al. | |
| 5,562,662 A | | 10/1996 | Brumfield et al. | |
| 5,782,831 A | | 7/1998 | Sherman et al. | |
| 5,910,141 A | * | 6/1999 | Morrison et al. | 606/61 |
| 6,050,997 A | | 4/2000 | Mullane | |
| 6,248,107 B1 | | 6/2001 | Foley et al. | |
| 6,251,111 B1 | * | 6/2001 | Barker et al. | 606/61 |
| 6,440,133 B1 | | 8/2002 | Beale et al. | |
| 6,648,888 B1 | | 11/2003 | Shluzas | |
| 2005/0137593 A1 | * | 6/2005 | Gray et al. | 606/61 |
| 2005/0192571 A1 | * | 9/2005 | Abdelgany | 606/61 |

* cited by examiner

*Primary Examiner*—Thomas C Barrett
*Assistant Examiner*—Andrew Yang
(74) *Attorney, Agent, or Firm*—Crompton, Seager & Tufte, LLC.

(57) ABSTRACT

Multifunction surgical devices and methods that can be used for implanting a spinal fixation system. Surgical devices of the invention can be used for positioning a bone engaging element with respect to a component of a spinal fixation system and for attaching the bone engaging element to the component of the spinal fixation system. Generally, surgical devices of the invention include a translating member and an attachment device. The translating member can be attached to a bone engaging element implanted in a vertebra, such as a pedicle screw or hook or the like. The translating member can be driven with a driving device to translate the bone engaging element with respect to a component of a spinal fixation system such as a connector or the like. The bone engaging element can be translated to an attachment position with respect to the connector or other component. An attachment device can then be used to attach the bone engaging element to the connector with a fastener such as a nut or the like.

16 Claims, 10 Drawing Sheets

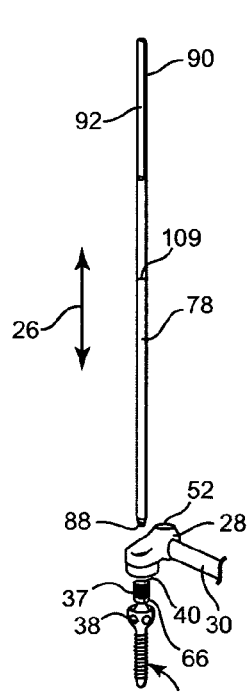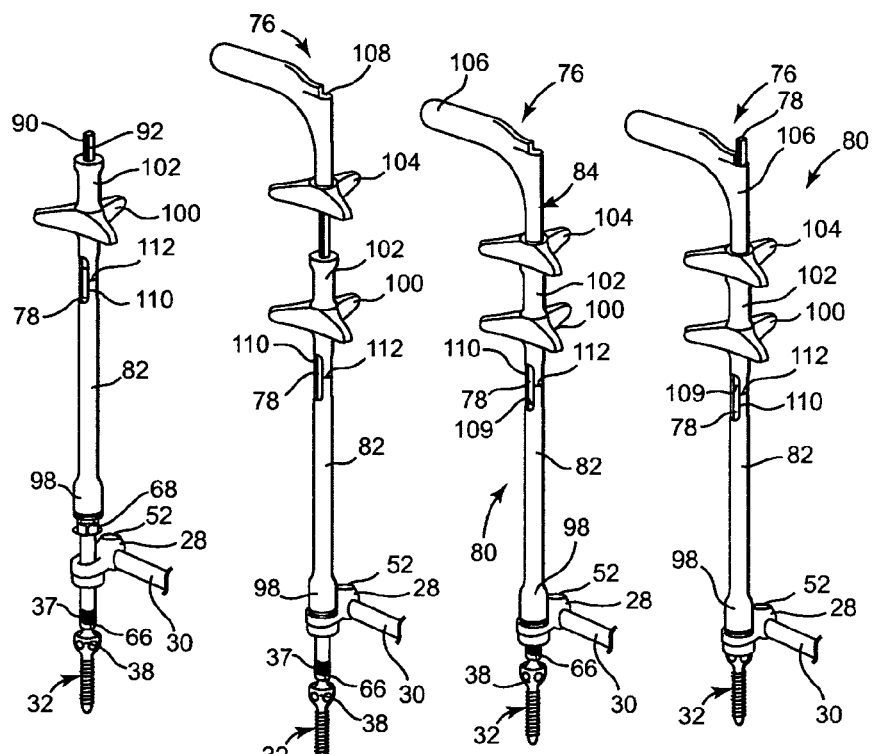
Fig. 12  Fig. 13  Fig. 14  Fig. 15  Fig. 16

SURGICAL DEVICES AND METHODS FOR VERTEBRAL SHIFTING UTILIZING SPINAL FIXATION SYSTEMS

FIELD OF THE INVENTION

The present invention relates generally to instruments used to manipulate selective vertabrae of the spine for spinal alignment and, in particular for reducing spondylolisthesis. More particularly, the present invention relates to the manipulation of bone engaging elements that are operatively engaged with the vertabrae for shifting one vertebra relative to another or the sacrum.

BACKGROUND OF THE INVENTION

Surgically implanted systems, such as fixation devices and apparatuses, are commonly used to correct a variety of back structure problems, including those that occur as a result of trauma or improper development during growth. A typical spinal fixation system generally comprises a support rod or system of support rods that are secured along at least a portion of the spine by bone screws or hooks or other bone engaging components. Such bone screws may be directly connected to the support rods or may be connected indirectly by using medial/lateral connectors or other similar components. The bone screws, bone hooks, medial/lateral connectors, and related items that function to anchor the support rods to the bones are often collectively referred to as bone engaging hardware or implants.

In a basic spinal fixation system, bone screws have a rod receiving opening extending through a head portion of each bone screw. The bone screws are secured in the vertebra at desired locations and a support rod is then extended through the opening in each bone screw. In order in order to fix the translational and rotational relationship of a support rod within the openings, set screws or caps are typically connected to the screw head as being threaded onto the screwhead or within a bore thereof and are tightened against the support rod. If needed, the support rod is bent or formed to support the spine in a desired manner or to exert the desired corrective or stabilizing forces to the spine. Such support rods may be pre-bent or bent during the procedure. For a spinal alignment correction with such systems, the shape of the support rods are utilized as the means for defining and maintaining the desired spinal curvature or vertebral alignment.

Other fixation systems have been developed that use medial/lateral connectors in association with bone screws to secure the support rods to the vertebra. The bone screws used in these systems typically include a threaded stud extending from the screw heads. The medial/lateral connectors include an arm and a head, and a rod receiving opening that extends through the head for connection to a support rod with a set screw or other locking device. The arm of the connector includes an opening, such as a hole or slot that can receive the threaded stud of a bone screw. A fastener can then be used to attach the bone screw to the medial/lateral connector. This type of system is utilized in correcting spinal structural deformities or abnormalities is the same general manner as the fixation system above described wherein the support rods are shaped to define and maintain a desired spinal alignment.

The fixation systems described above are commonly utilized for defining and maintaining a desired spinal structural alignment, but are not used for creating a motive force to move or shift one vertebra relative to another. Such force creation is typically performed as a distinct procedure. The motive force can be provided manually, such as by the surgeon physically manipulating a vertebra to permit connection of an implant within a vertebra to a pre-bent support rod, or by other drive device utilization, with the purpose of any such manipulation or utilization being to cause some sort of movement or shifting of one or more vertebra to create a desired spinal structural alignment.

The shifting of one or more vertebra for the purpose of at least partially correcting a spinal structural deformity or abnormality, whether as a result of injury, trauma, or a congenital condition, is often referred to as a reduction process or technique. A reduction is any movement toward any healthy, normal, or efficient position as may be determined for any patient. Certain deviations or pathologies from such normal positions are characterized according to the relative directional shifting between adjacent vertebra. Pathologies include, among other things, spondylolisthesis (a front to back misalignment of a vertebral body on another or the sacrum) and, scoliosis (a lateral misalignment of a vertebral body on another of the sacrum).

Reduction techniques include manual methods, where a surgeon provides the requisite force to a vertebra which may include the use of a tool, and device methods, where such a force is generated, compounded, or converted in one way or another for application to a vertebra.

In one type of manual procedure, a spinal fixation system such as described above is used within a reduction process of a vertebra. By such a reduction process, a vertebra is reduced to a more normal anatomical position or other desired position relative to adjacent vertebra and held in place by the implant system. Usually, one or more bone screws are implanted in a vertebra adjacent to a vertebra to be reduced. A shaped support rod is then attached to the bone screw such as may include a medial/lateral connector so that the rod cantilevers over the vertebra to be reduced or bridges a vertebra to be reduced. This process can be repeated so that rods are implanted on opposite sides of a vertebra to be reduced. Next, a bone screw is implanted in the vertebra for connection to the support rod positioned away from the bone screw. Typically, the rod is pre-shaped to position the bone screw connector or medial/lateral connector in a position that will locate the vertebra to be reduced in a desired position. However, the vertebra must be moved or translated so that the bone screw implanted in the vertebra can be attached to the medial/lateral connector such as by manual movement by the surgeon with or without use of a tool.

Devices and methods have also been developed for translating a vertebra relative to another where a force for causing such movement is generated, compounded, or converted by the device for application of the force to one or more vertebra. Typically, a drive force may be provided by a surgeon, which force operates the device mechanism for creating a force to translate a vertebra. Such devices are known to grab a vertebra by way of a hook or screw that may be implanted. Generally, these devices grasp a vertebral portion or an implanted bone engaging element and pull it toward a fixed element either of the device or other support system. Devices have been developed recently that utilize hooks or implants of a spinal fixation system as a bone engaging element for grasping a vertebra and to move it relative to a support rod of the spinal fixation system. See U.S. Pat. No. 5,219,349 to Krag et al, U.S. Pat. No. 5,562,662 to Brumfield et al, U.S. Pat. No. 5,782,831 to Sherman et al, U.S. Pat. No. 5,910,141 to Morrison et al, U.S. Pat. No. 6,248,107 to Foley et al, and U.S. Pat. No. 6,440,133 to Beale et al. Although these devices can be effective for translating such a bone engaging element, they are generally complex and cumbersome to use, especially in the confined spaces available for these types of spinal surgeries. Moreover, these devices require distinct techniques for attaching a bone engaging element to a component of a spinal fixation system and for moving the bone engaging element into a desired position.

SUMMARY OF THE INVENTION

The present invention provides multifunction surgical devices that can be used for implanting a spinal fixation system. In particular, surgical devices of the invention can be used for positioning a bone engaging element with respect to a component of a spinal fixation system and for attaching the bone engaging element to the component of the spinal fixation system. For example, devices of the invention can be attached to a bone engaging element implanted in a vertebra, such as a pedicle screw or hook or the like, and used to translate the bone engaging element with respect to a component of a spinal fixation system such as a medial/lateral connector or the like thereby moving the vertebra to which it is attached. As such, the bone engaging element can be translated to an attachment position with respect to the connector or other component. Also, devices of the invention can be used to attach the bone engaging element to the connector with a fastener such as a nut or the like. Thus, in accordance with the invention, a bone engaging element implanted in a vertebra can be translated to an attachment position and attached to a component of a spinal fixation system with the same tool.

In one aspect of the invention, a multifunction surgical device is provided. The device can be used for positioning a bone engaging element with respect to a component of a spinal fixation system and for attaching the bone engaging element to the component of the spinal fixation system while engaging the surgical device with the spinal fixation system. Generally, the surgical device includes a translating member, means for driving the translating member, and means for attaching a fastener to a bone engaging element removably engaged with the translating member.

The translating member includes a reduction axis and preferably has an attachment device at a distal end. Preferably the attachment device is capable of detachably engaging a bone engaging element implanted in a vertebra. For example, the attachment device may include a threaded portion, such as a stud, that can be engaged with a threaded portion of a bone engaging element such as a tapped hole of a pedicle screw or the like.

The means for driving the translating member preferably comprises means for axially driving the translating member along the reduction axis. As such, a bone engaging element removably engaged with the attachment device of the translation member and implanted in a vertebra can be translated to an attachment position with respect to a component of a spinal fixation system. In preferred aspects of the invention, the means for driving the translating member may comprise a driving device that can be used to engage a threaded portion of the translating member. For example, a driving device can be used to engage a fastener threadingly engaged with the threaded portion of the translating member for driving the fastener against a component of a spinal fixation system thereby driving the translating member.

The means for attaching a fastener to a bone engaging element can comprise a fastener driving device. In an aspect of the invention the fastener driving device comprises a driving device that is coaxial with the translating member and includes a fastener engaging portion such as a socket that can engage a nut or the like. In another aspect of the invention, both the means for driving the translating member and the means for attaching a fastener comprise a driving device capable of driving a fastener or the like along a threaded portion of the translating member.

In another aspect of the invention, a multifunction surgical device is provided. The device can be used for positioning a bone engaging element with respect to a component of a spinal fixation system and for attaching the bone engaging element to the component of the spinal fixation system while engaging the surgical device with the spinal fixation system. Generally, the surgical device includes a translating member and a driving and attaching device for driving the translating member and for attaching a fastener to a bone engaging element removably engaged with the translating member.

The translating member includes a reduction axis and preferably has an attachment device at a distal end. Preferably the attachment device is capable of detachably engaging a bone engaging element implanted in a vertebra. For example, the attachment device may include a threaded portion that can be engaged with a threaded portion of a bone engaging element such as a pedicle screw or the like.

Preferably, the driving and attaching device is capable of axially driving the translating member along the reduction axis. In one aspect of the invention, the driving and attaching device can be coaxial with the translating member. The driving and attaching device is also preferably capable of attaching a fastener to the bone engaging element removably engaged with the translating member. Thus, a bone engaging element that is removably engaged with the attachment device of the translating member and implanted in a vertebra can be driven to an attachment position with respect to a component of a spinal fixation system with the driving and attaching device and attached to the component with a fastener or the like.

In another aspect of the invention, a method for positioning and attaching a bone engaging element to a component of a spinal fixation system is provided. That is, a bone engaging element implanted in a vertebra can be positioned with respect to a component of a spinal fixation system and attached to the component of the spinal fixation system by methods of the invention. Generally, such a method includes steps of engaging a spinal fixation system with a multifunction device, removably attaching a translating member of the device to a bone engaging element, driving the translating member, and attaching a fastener to the bone engaging element with the multifunction surgical device.

A step of engaging a spinal fixation system with a multifunction device preferably comprises engaging a component of a spinal fixation system with a multifunction surgical device comprising a translating member having a reduction axis and a driving and attaching device capable of driving the translating member along the reduction axis and attaching a fastener to the bone engaging element.

A step of attaching the translating member of the multifunction surgical device preferably comprises removably attaching the translating member to a bone engaging element implanted in a vertebra. In one aspect of the invention, the translating member is attached a bone engaging element such that a threaded portion of the translating member is aligned with a threaded portion of the bone engaging element. Preferably, a threaded portion of the translating member is aligned with a threaded portion of the bone engaging element such that a continuous thread is formed wherein a fastener such as a nut or the like can uninterruptedly pass from the detachable translating member to the bone engaging element.

A step of driving the translating member preferably comprises translating the bone engaging element with respect to the component of the spinal fixation system by driving the translating member along the reduction axis with the driving and attaching device of the multifunction surgical device. Also, a step of attaching a fastener preferably comprises attaching a fastener to the bone engaging element with the driving and attaching device of the multifunction surgical device.

In another aspect of the invention, an anchoring device for use with a spinal fixation system is provided. Such an anchoring device can be used with a spinal fixation system including at least one spine stabilizing rod and at least one connector for attaching the spine stabilizing rod to the anchoring device. The anchoring device generally includes a bone engaging portion and a reduction and attachment device. The reduction and attachment device preferably extends from the bone engaging portion and comprises first and second threaded portions extending along a reduction axis. The first threaded portion is preferably spaced apart from the bone engaging portion. The second threaded portion is preferably detachably engaged with the first threaded portion. The second threaded portion is also preferably rotationally aligned with the first threaded portion such that the threads of the second threaded portion align with and uninterruptedly continue the threads of the first threaded portion.

The reduction and attachment device is preferably capable of being positioned relative to a connector of a spinal fixation system such that a fastener can be driven along the second threaded portion and against the connector for translating the bone engaging portion along the reduction axis. Preferably, the fastener can uninterruptedly pass from the second threaded portion to the first threaded portion for attaching the anchoring device to the connector.

BRIEF DESCRIPTION OF THE DRAWINGS

The accompanying drawings, which are incorporated in and constitute a part of this application, illustrate several aspects of the invention and together with a description of the embodiments serve to explain principles of the present invention. A brief description of the drawings is as follows:

FIG. 12 is a perspective view of another translating member of a surgical device in accordance with the present invention positioned relative to a spinal fixation system having a bone screw to be implanted in a vertebra to be reduced and a connector attached to a support rod that is fixed in position;

FIG. 13 is a perspective view of a surgical device in accordance with the present invention having a translating member attached to a bone screw to be implanted in a vertebra to be reduced and a driving and attaching device including a nut driver with a window for monitoring an indicator mark of the translating member to determine the relative position of the translating member to the driving and attaching device;

FIG. 14 is a perspective view of the surgical device of FIG. 13 wherein another driving and attaching device in accordance with the present invention of a surgical device is engaged with a connector for translating the translating member and bone screw with respect to the connector;

FIG. 15 is a perspective view of the surgical device of FIGS. 13 and 14 showing the bone screw as translated by the surgical device to a position closer to the connector than that of FIG. 14, which position can be monitored through the window of the driving and attaching device;

FIG. 16 is a perspective view of the surgical device of FIGS. 13-15 showing the bone screw in a seated position with respect to the connector;

DETAILED DESCRIPTION

In general, the present invention provides devices and methods for manipulating components of a spinal fixation system for the purpose of shifting at least one vertebra relative to another, with particular applicability for reducing at least one vertebra toward a normal, healthy or more efficient position. More particularly, the present invention provides devices and methods for positioning a bone engaging or grasping element with respect to another component of a spinal fixation system such as a support rod and then to attach the bone engaging element to the component of the spinal fixation system. For example, a device of the invention can be used to engage a bone screw implanted in a vertebra, translate the bone screw to reduce the vertebra toward a desired corrective position, position the bone screw in an attachment position with respect to another component of a spinal fixation system, and attach the bone screw to the other component directly or indirectly. Advantageously, a bone screw or the like can be translated to an attachment position and attached to a component of a spinal fixation system with the preferred devices in accordance with the present invention.

Figure 1:
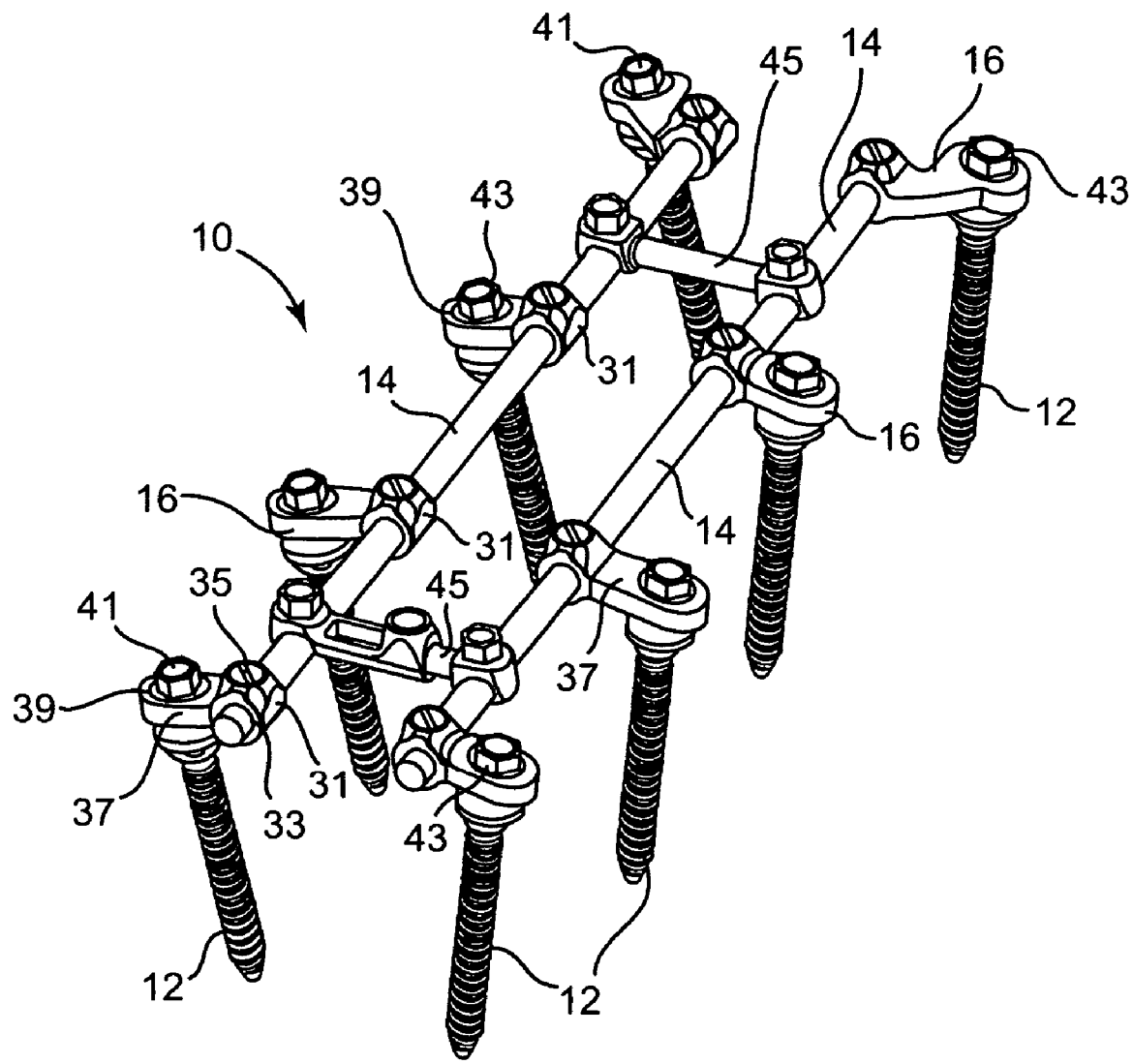
FIG. 1 is a perspective view of a spinal fixation system including components to which forces can be transmitted for translating one or more vertebra in accordance with the present invention, the spinal fixation system having bone engaging elements comprising bone screws that can be implanted in vertebrae and that are attached to support rods by medial/lateral connectors.

In FIG. 1, a spinal fixation system 10 is illustrated that can be assembled and utilized in reduction techniques and devices in accordance with the present invention. Also, U.S. Pat. No. 6,050,997 granted to Mullane on Apr. 18, 2000 and assigned to the Assignee of the present invention describes spinal fixation systems of a similar type, which disclosure is fully incorporated herein by reference. The illustrated spinal fixation system 10 includes plural bone engaging or grasping elements shown as bone screws 12; however, other bone engaging or grasping elements such as hooks or the like could be used instead. To be usable in accordance with the present invention, any means of fixing a bone engaging element to a vertebra, whether permanent or temporary is contemplated, including threaded screws, cables, hooks, or other mechanical fasteners, or that use bonding techniques or the like including adhesives or weld materials. Moreover, the engagement may not require any actual connection or means to do so, such as where vertebral shifting merely requires the application of a force in a direction causing engagement of respective surfaces. As shown, the bone screws 12 are used to anchor the spinal fixation system 10 to vertebrae of a spine (not shown). Usually, the bone screws 12 are implanted in a bilateral posterior configuration to a spine such as by implanting the bone screws 12 into the pedicle processes of certain vertebra of the spine. The spinal fixation system 10 also includes support rods 14 that can be shaped to define a predetermined spinal curvature or alignment. As such, the illustrated spinal fixation system 10 can be used to define and maintain a desired spinal alignment.

In accordance with the illustrated embodiment, the support rods 14 are connected to the bone screws 12 by medial/lateral connectors 16. In other spinal fixation systems, bone engaging elements can be connected to supports rods without the use of medial/lateral connectors such as by using a clamp or saddle type of device to connect a bone engaging element directly to a support rod. Other indirect connectors than the medial/lateral connectors 16 are also contemplated. The illustrated medial/lateral connector 16 includes a head 31 that has a passage 33 that can receive a support rod 14. As such, the medial/lateral connector 16 can translate longitudinally along a direction of extension of the support rod 14 and preferably can also rotate around the support rod 14. This allows the medial/lateral connector 16 to be positioned in varying positions with respect to the support rod 14. A set screw 35 or other fastening device can be used to secure the medial/lateral connector 16 to the support rod 14 at any desired orientation with respect to the support rod 14. The medial/lateral connector 16 also includes an arm 37 extending from the head 31, as illustrated. The arm 37 includes a slot 39 that can receive a stud 41 of the bone screw 12. As shown, a nut 43 can then be used to attach the bone screw 12 to the medial/lateral connector 16. Additionally, a transverse bridge connector 45 is illustrated that can be used to connect a pair of support rods 14 at one or more desired locations along their longitudinal length for providing additional structural support or rigidity, if desired.

In accordance with an aspect of the present invention, a spinal fixation system, such as the illustrated spinal fixation system 10 can be advantageously utilized as part of techniques described below for moving the position of one or more vertebra laterally with respect to another vertebra. Such a correction is commonly called a reduction. By reduction, a vertebra is moved laterally toward a healthy, normal, or efficient position as may be determined for any patient. A vertebra may be fully restored to a normal anatomical position by a single adjustment or in stages. For example, in a first procedure a vertebra may be moved a portion of the distance required to position the vertebra in a normal anatomical position. In one or more subsequent procedures, the vertebra may be moved by additional amounts thereby moving the vertebra closer to a desired location for the vertebra. In accordance with the present invention, a spinal fixation system 10 can be used with surgical devices and methods described below to correct spinal pathologies including, as non-limiting examples, spondylolisthesis and scoliosis. Such surgical devices and methods in accordance with the present invention can also be used to correct spinal misalignment due to injury or trauma to the spine.

Such spinal pathologies and/or injuries are commonly characterized by having one or more vertebra out of position with respect to a normal anatomical position. As such, these vertebrae are shifted out of plane to a normally balanced spine with respect to each other. For example, referring to FIG. 2, a vertebra 18 is shown with respect to adjacent vertebra 11 and 13. As illustrated, the vertebra 11 and 13 are positioned in a normal anatomical position and the vertebra 18 is out of place with respect to a normal anatomical position for the vertebra 18. A normal anatomical position would be one where the vertebra 18 is positioned with respect to the vertebra 11 and 13 so as to follow a normal spinal curvature.

Figure 2:
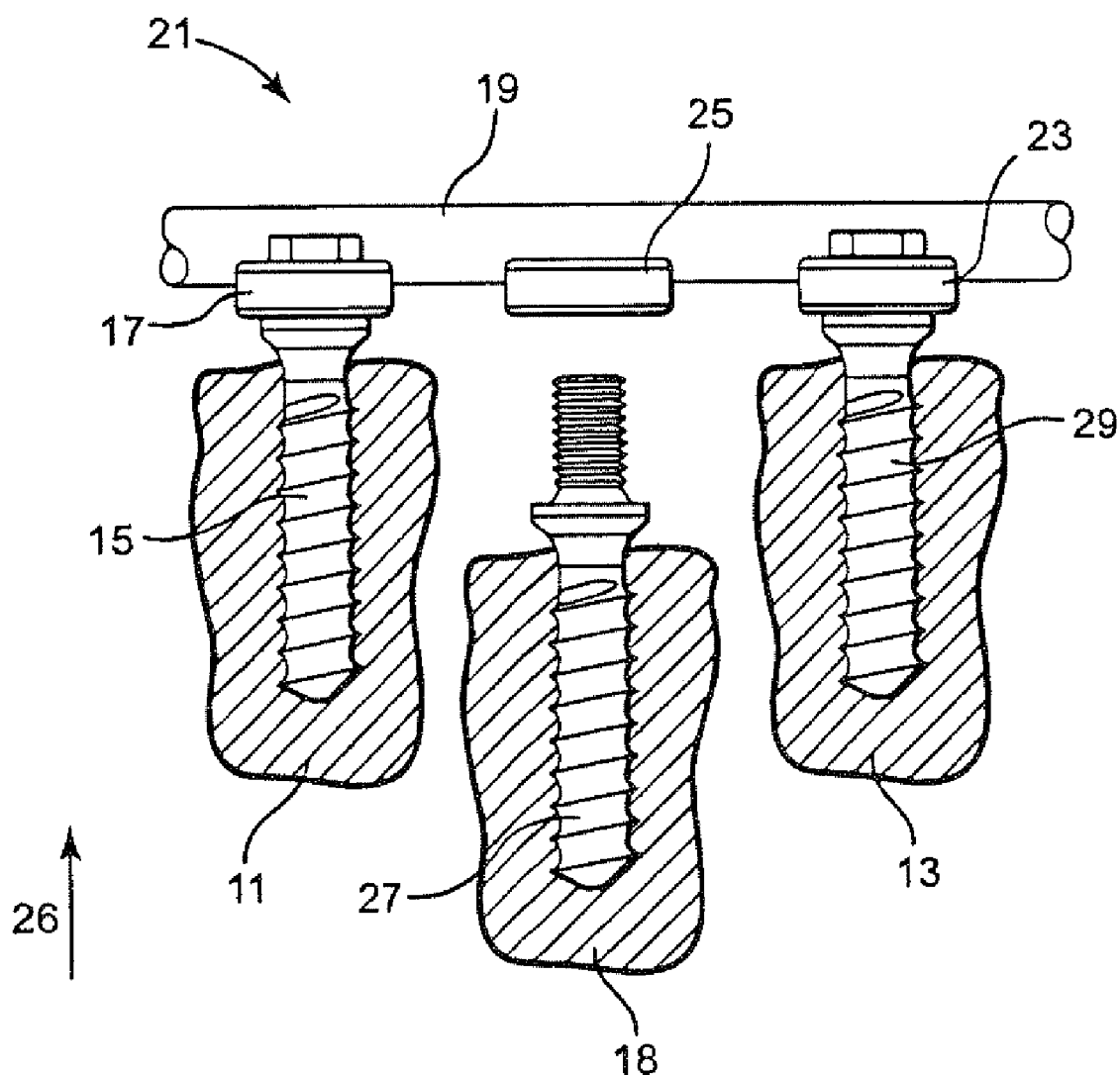
FIG. 2 is a side view of components of a spinal fixation system including a bone screw implanted in a vertebra to be reduced and bone screws implanted in adjacent vertebra on both sides thereof that are further connected with a support rod.

A surgical procedure can be used to reduce the vertebra 18 toward a normal anatomical position with respect to the vertebra 11 and 13. In FIG. 2, a spinal fixation system 21 is illustrated with respect to vertebrae 11, 13 and 18 as such spinal fixation system 21 would be viewed from one side of the spine, but with the vertebrae in cross-section to show bone engaging elements 15, 29 and 27 as implants. As shown, vertebra 11 includes an implanted bone screw 15 that is attached to a connector 17, which is further attached to a support rod 19. Vertebra 13 includes an implanted bone screw 29 that is attached to a connector 23, which is further attached to the support rod 19. A connector 25 is also shown connected to the support rod 19 for receiving a bone screw 27 implanted in the vertebra 18 that is to be reduced. In accordance with one aspect of the present invention, it is desirable to translate the displaced vertebra 18 with respect to the others by controllably moving the bone screw 27 (as a bone engaging element) relative to the support rod 19 (as a fixed element of a spinal fixation system).

In order to attach the bone screw 27 to the connecter 25, the bone screw 27 is to be translated with respect to the medial/lateral connector 25 as an extension of the support rod 19. In accordance with the present invention, such a bone screw 27 is grasped with a tool or device and pulled toward the connector 25 preferably until it can be attached to the connector 25 or directly to a support rod 19 (for a system that does not use connectors). Such action in this case, utilizes an axially directed force exerted by a tool against an upper surface of the connector 25 (or rod 19 directly or indirectly) while pulling the bone screw 27 through a hole of the connector 25. Any such tool or device can otherwise be operatively fixed in the axial direction to the connector 25 (or rod 19 directly or indirectly) or positioned to utilize an axial force exerted opposite to the direction of movement of the bone engaging element to facilitate such movement. Alternatively, the bone screw 27 could be pushed to increase the space between the screw 27 and support rod 19, such as may be accomplished by operatively fixing the tool or device to the connector 25 (or the rod 19 directly or indirectly) in the axial direction or by positioning such a tool or device to exert an axial force against the movement direction, e.g. to the bottom surface of the connector 25. The present invention provides surgical devices and methods that can be used to engage a bone screw implanted in or other bone engaging element engaged with a vertebra to be reduced, to translate the bone screw, preferably to an attachment position with respect to a component of a spinal fixation system such as a medial/lateral connector or support rod, and to attach the bone engaging element to the component. Examples of such devices and methods are described in more detail below.

In FIGS. 3 through 7, one method of reducing a vertebra in accordance with the invention is illustrated. Method steps are illustrated with respect to an embodiment of a surgical device of the present invention and certain components of a spinal fixation system that are described below. A surgical device 20 in accordance with the present invention is shown in FIGS. 4-7. The surgical device 20 preferably includes a translating member 22 and a driving and attaching device 24. The driving and attaching device 24 can advantageously be used to translate the translating member 22 in a reduction direction 26 (either by pulling or pushing as such axial fixation or force exertion is effectively controlled) and also to attach a bone engaging element to a component of a spinal fixation system, as described below.

Figure 3:
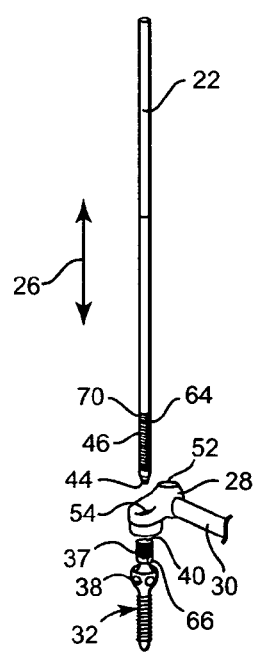
FIG. 3 is a perspective view of a translating member of a surgical device in accordance with an aspect of the present invention positioned relative to a spinal fixation system having a bone screw to be implanted in a vertebra to be reduced and a connector attached to a support rod that is fixed in position.

With reference to FIG. 3, a medial/lateral connector 28 is shown attached to a support rod 30 of a spinal fixation system. For example, the medial/lateral connector 28 and support rod 30 may be similar to the medial/lateral connector 25 and support rod 19 as shown in FIG. 2 and described above. As illustrated, the medial/lateral connector 28 is spaced apart from a bone screw 32 that would be implanted in a vertebra to be reduced (not shown). For example, referring back to FIG. 2, the bone screw 32 would be the bone screw 27 implanted in vertebra 18 that is to be reduced. In order to move a vertebra attached to the bone screw 32 to a desired position, the bone screw 32 is to be moved toward an attachment position so that it can be attached to the medial/lateral connector 28. The surgical device 20 can advantageously be used to both move the bone screw 32 to such an attachment position and to attach the bone screw to the medial/lateral connector 28 as described below.

Figure 6:
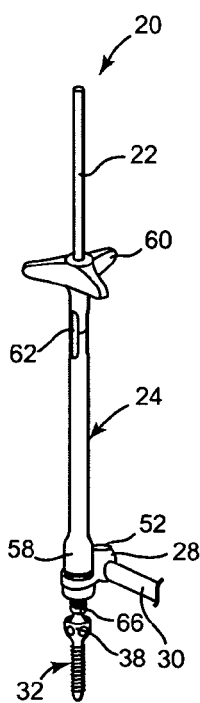
FIG. 6 is a perspective view of the surgical device of FIGS. 4 and 5 showing the bone screw as translated by the surgical device to a position closer to the connector than that of FIG. 5.
Figure 7:
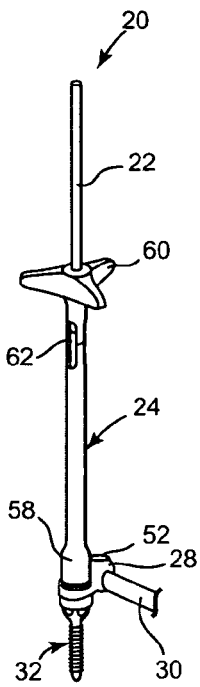
FIG. 7 is a perspective view of the surgical device of FIGS. 4-6 showing the bone screw in a seated position with respect to the connector.
Figure 8:
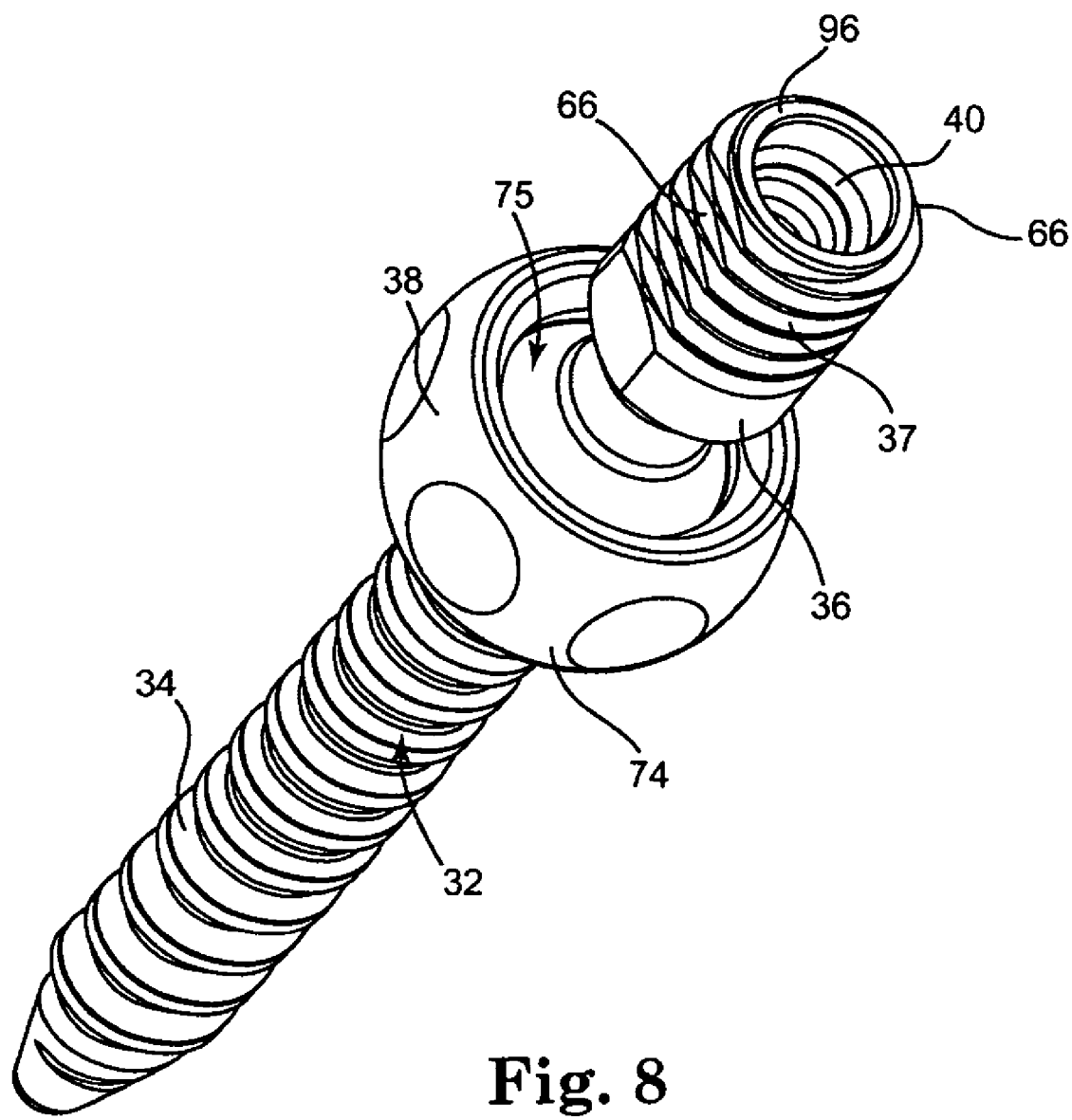
FIG. 8 is a perspective view of a bone screw of the spinal fixation system of FIG. 1 having a coarse threaded portion for implanting the bone screw in bone and a threaded stud for attaching the bone screw to a connector of a preferred spinal fixation system and a tapped hole in the threaded stud for attaching a surgical device in accordance with the present invention to the bone screw.

Referring to FIG. 8, the bone screw 32 that is shown in FIGS. 3-7 is shown in greater detail as such bone screw 32 can be connected with the translating member 22 of the surgical device 20 to translate the bone screw 32. As above, any means of engaging a vertebra, such as may or may not be implanted in the vertebra, is contemplated. Moreover, one example of a means for connecting the screw 32 to the translating member 22 is described below with an understanding that other mechanical connectors are contemplated having the ability to be detached. As illustrated, the exemplary bone screw 32 includes a course-threaded portion 34 for implanting the bone screw 32 in a vertebra as such implant techniques are well known. The bone screw 32 also includes a stud 36 having a threaded portion 37 (thereby forming a threaded stud) that can be used for attaching the bone screw 32 to the medial/lateral connector 28. As illustrated, the threaded stud 36 extends from a ball and socket joint 38 that provides for rotational and angular motion between the stud 36 and the course-threaded portion 34 in a manner as known and described in U.S. Pat. No. 6,050,997 to Mullane that is incorporated by reference herein. The threaded stud 36 also preferably includes a tapped bore 40 that can be used for attaching the translating member 22 to the bone screw 32 as described below. The ability to functionally engage a vertebra to translate a force to move that vertebra and to connect with a translating member 22 are the minimal requirements of a bone engaging element in accordance with this embodiment. It is preferable to use an element that is further a functional component of the spinal fixation system to be left on the respective vertebrae after a reduction in accordance with methods of the present invention.

Figure 9:
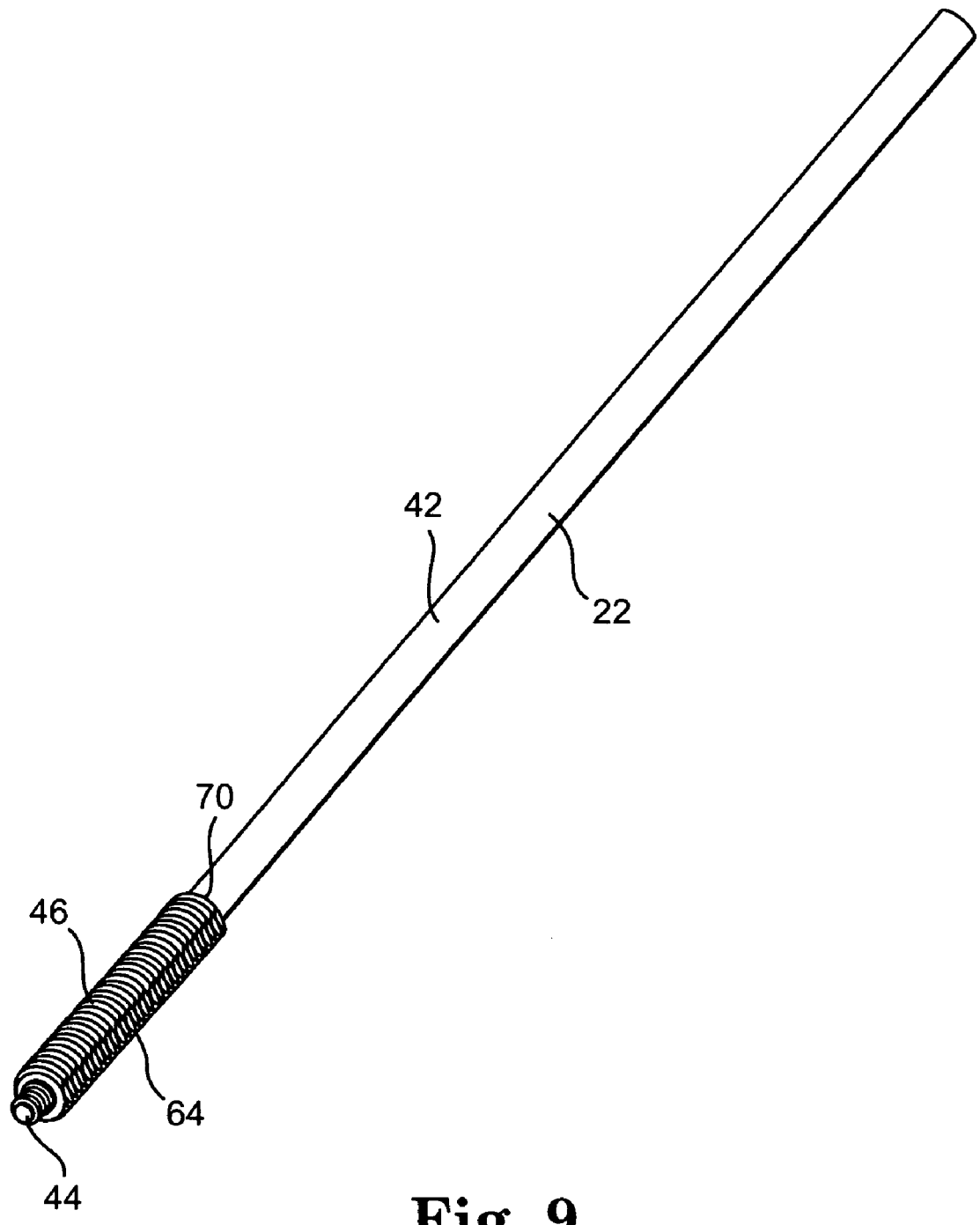
FIG. 9 is a perspective view of a translating member of the surgical device of FIGS. 4-7 showing a threaded portion adjacent to a distal end thereof and a threaded boss extending from the distal end thereof.

As shown in FIG. 9, the translating member 22 preferably comprises a linearly extending shaft 42. The shaft 42 preferably includes a threaded boss 44 extending from the distal end of the shaft 42 and a threaded portion 46 adjacent the distal end of the shaft 42. Preferably, the threaded boss 44 functions as an attachment component that can be engaged with the tapped bore 40 of the bone screw 32 for attaching the translating member 22 to the bone screw 32. In accordance with the invention, the translating member 22 can be attached to a bone engaging element in any manner so that the translating member 22 is controllably detachable from the bone engaging element. For example, mechanical devices or mechanisms such as spring loaded attachment devices, bayonet style connector devices, and other releasable devices and the like may be used. Such a connection preferably permits translation of the bone engaging element in both linear directions.

In accordance with the present invention, the threaded portion 37 of the stud 36 of the bone screw 32 and the threaded portion 46 of the translating member 22 preferably provide a continuous threaded portion when the translating member 22 is attached to the stud 36 of the bone screw 32. As such, the threaded portion 37 of the stud 36 is threadingly aligned or timed with the threaded portion 46 of the translating member 22 when the boss 44 of the translating member 22 is fully screwed into bore 40 of the bone screw 32 (i.e. when the distal end of shaft 42 seats with the top surface of stud 36). Thus, when the translating member 22 is attached to the stud 36 of the bone screw 32, the threads of the threaded portion 46 of the translating member 22 can line up with the threads of the threaded portion 37 of the stud 36 to effectively form a continuous threaded portion. As such, a nut can uninterruptedly pass from the threaded portion 46 of the translating member 22 to the threaded portion 37 of the stud 36. By driving a nut (not shown) onto the threaded stud 37, the nut can be used to attach the bone screw 32 to the medial/lateral connector 28 when the bone screw 32 is positioned in an attachment position with respect to the medial/lateral connector 28, as described below.

Figure 10:
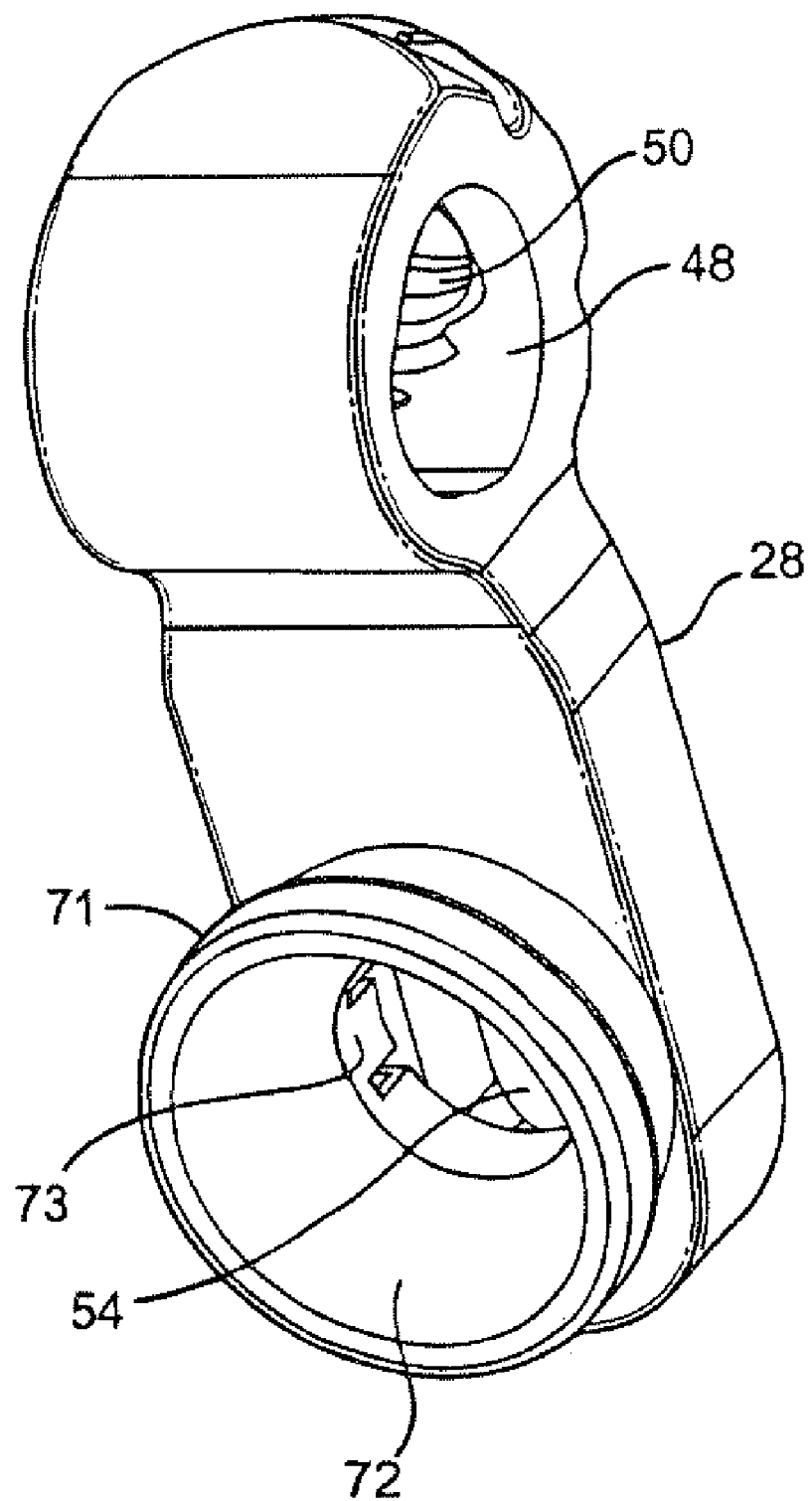
FIG. 10 is a perspective view of a connector of the spinal fixation system of FIG. 1 showing an opening for receiving a support rod of a spinal fixation system and a slot for receiving a bone screw to be attached to the connector.

Next referring to FIG. 10, the medial/lateral connector 28 of FIGS. 3-7 is illustrated in greater detail. As shown, the medial/lateral connector 28 includes a passage 48 that can slidingly receive the support rod 30. The medial/lateral connector 28 also includes a tapped hole 50 that can be used to secure the medial/lateral connector 28 to the support rod 30 with a fastener such as a set screw 52 or the like (see FIG. 3). The medial/lateral connector 28 also includes an opening 54 that can receive the threaded stud 36 of the bone screw 32. As such, the threaded stud 36 of the bone screw 32 can pass through the opening 54 of the medial/lateral connector 28 and be attached thereto by using a fastener such as a nut 68 or the like. A more specific description of a medial/lateral connector is provided in U.S. Pat. No. 6,050,997 to Mullane that is fully incorporated herein by reference.

Preferably, the opening 54 is designed to also restrict or prevent rotation of the threaded stud 36 of the bone screw 32 or the translation member 22 when either is positioned in the opening 54. As shown, the opening 54 preferably comprises a slot that has a width to allow the threaded stud 36 to pass through the opening 54 with flats 66 of the threaded stud 36 aligned relative to corresponding flat surface portions defining the width of the opening 54. That is, the distance between the flats 66 is slightly less than the width of the slotted opening 54 so that the threaded stud 36 can pass through the opening 54 in a direction of extension of the threaded stud 36 but cannot rotate with respect to the opening 54. Likewise flats 64 are preferably provided on the threaded portion 46 of the translating member 22 for restricting or preventing rotation of the translating member 22 with respect to the slotted opening 54 when the threaded portion 46 of the translating member 22 is positioned within the slotted opening 54. A seat portion 71 is also shown having a seat surface 72 designed to fit with ball portion 74 of bone screw 32 and as also fitted partially within slot 54. An opening 73 permits the threaded stud 36 or translation member 22 to pass through and still be limited from rotation by surfaces of the slot 54 as described above. A compressive force created by a nut 68 threaded to the stud 36 when positioned within opening 73 and slot 54 is sufficient to secure the components in place.

Figure 11:
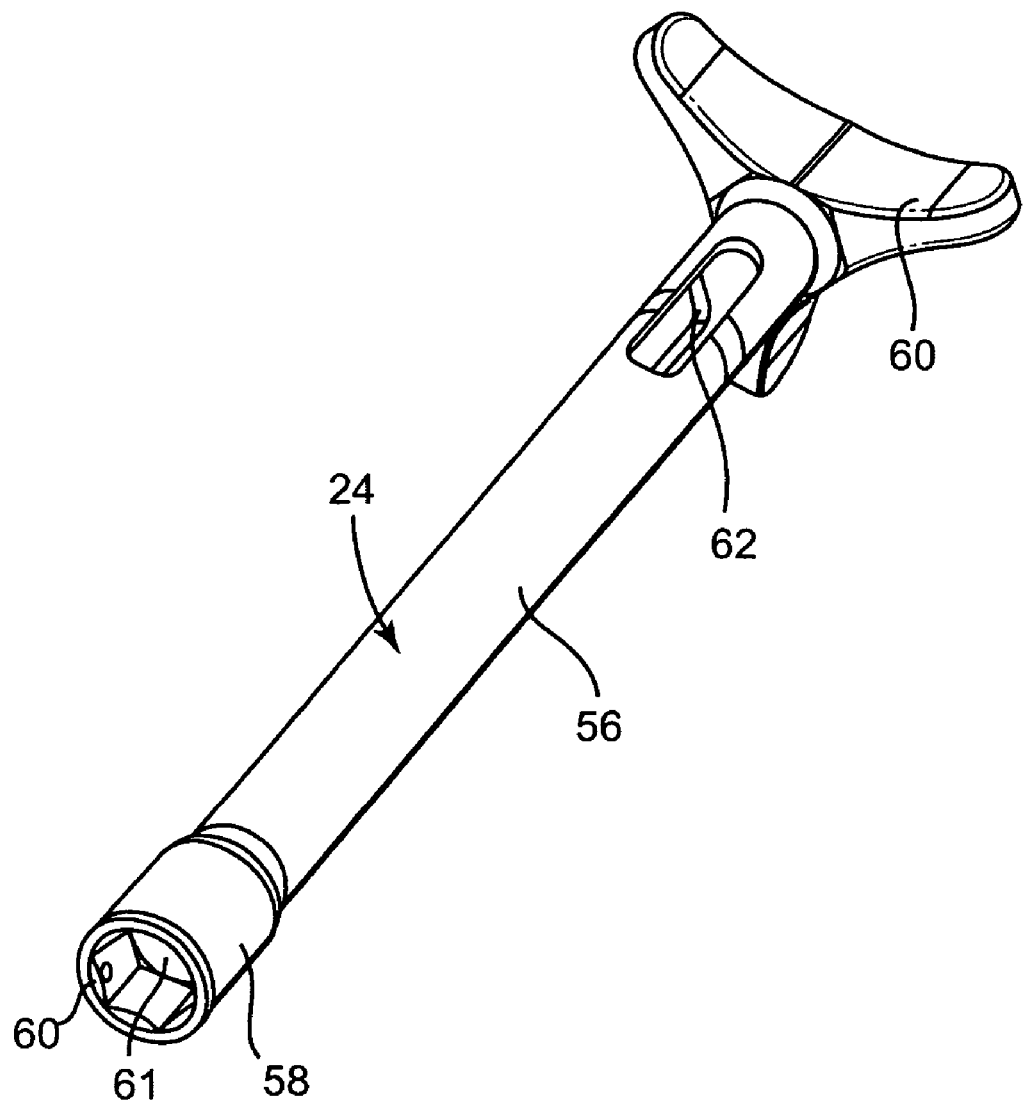
FIG. 11 is a perspective view of components of one embodiment of a driving and attaching device in accordance with the present invention showing a socket, a handle, and an indicator window.

In FIG. 11, the driving and attaching device 24 is illustrated in more detail. As is discussed in further detail below, the driving and attaching device 24 preferably has the capability to provide multiple functions. Firstly, the driving and attaching device 24 can preferably be used to drive or translate the translating member 22 along a direction of extension of the translating member 22. Additionally, the driving and attaching device 24 can also preferably be used to attach the bone screw 32 to the medial/lateral connector 28 by driving a nut 68 onto the threaded stud 36 of the bone screw 32 when the threaded stud 36 is positioned in the opening 54 of the medial/lateral connector 28.

Preferably, the driving and attaching device 24 comprises a cannulated or tube like body 56 having a socket 58 at a distal end and a handle 60 spaced from the distal end that can be used to rotationally drive the body 56 and thus the socket 58. The body 56 of the driving and attaching device 24 also preferably includes a longitudinal passage 61 for receiving the translating member 22 so that the translating member 22 can linearly translate and rotate with respect to the body 56 of the driving and attaching device 24. The passage 61 preferably comprises a bore that passes entirely through the body 56. Thus, the body 56 of the driving and attaching device 24 can be slid over the translating member 22 (as can be seen in FIGS. 4-7) thus positioning the translating member 22 through the driving and attaching device 24 so that the body 56 may rotate with respect to the translating member 22 while the translating member 22 is extended through and rotationally limited by the opening 54 of connector 28 and connected with the tip bone screw 32. It is noted that, the body 56 of the driving and attaching device 24 and/or the translating member 22 may include bearing surfaces, elements or guide surfaces to facilitate linear and/or rotational movement between the body 56 of the driving and attaching device 24 and the translating member 22.

In operation, the handle 60 can be used to rotate the body 56 and thus socket 58 for driving a fastener such as the nut 68 (see FIG. 4) along the threaded portion 46 of the translating member 22. Continued advancement of the nut 68 after it engages the connector 28 will in turn drive the translating member 22 along the reduction direction 26 (see FIGS. 5 and 6). Such driving of the nut 68 can therefore cause the bone screw 32 that is attached to the translating member 22 (and a vertebra attached thereto) to move along the reduction direction 26.

Preferably, the socket 58 includes a capture device 63 that can be used to releasably hold a nut 68 within the socket 58. As shown, the capture device 63 comprises a spring-loaded button as may be conventionally provided but can be any device capable of releasably capturing and holding a nut within the socket 58. The driving and attaching device 24 also preferably includes a window portion 62 provided through the body 56 that can be used to view the position of the translating member 22 so that the position of the bone screw 32 with respect to the medial/lateral connector 28 can be determined as described below.

The above-described surgical device 20 can be used to reduce a vertebra attached to the bone screw 32 as illustrated in FIGS. 3-7 and in accordance with the present invention. As discussed above, bone screws can be implanted, for example, as a bi-lateral posterior configuration wherein the bone screws are implanted in the pedicle processes of a vertebrae of the spine. In a typical spinal fixation system (see FIG. 1), such a configuration can include multiple vertebra connected by support rods that are attached to the vertebra by bone screws implanted on both sides of the spinal process. In FIGS. 3 through 7 a method of reducing a vertebra with the surgical device 20 is described with respect to one side of a spinal fixation system. That is, use of the surgical device 20 is described with reference to an attachment location that includes a medial/lateral connector 28 for attaching a bone screw 32 to the medial/lateral connector 28. It is understood, however, that multiple surgical devices 20 may be used, such as by using one on each side of a vertebra to be reduced. In some processes multiple devices 20 can be used simultaneously to bi-laterally reduce a vertebra. In other processes, a single device or multiple devices can be used for bi-lateral adjustment that can be conducted by alternating from side to side with incremental reduction. That is, a vertebrae may be reduced from one bi-lateral position by a small amount and then reduced at the other bi-lateral position by a small amount, which process can be repeated until the desired reduction is complete. A single device can be moved side-to-side or multiple devices can be used in alternating manner.

Now, referring to FIG. 3, the support rod 30 is shown extending from the medial/lateral connector 28. Preferably, the support rod 30 is further connected to another connector (not shown) that is attached to a bone screw implanted in a vertebra. For example, referring to FIG. 2, the medial/lateral connector 28 could be similar to the connector 25, which is connected by rod 19 to an adjacent connector 17 that is attached to bone screw 15 implanted in vertebra 11. Thus, as can be seen in FIG. 2, the connector 25 is in a fixed position with respect to the spinal fixation system 21 and can provide a stable fixed component of the spinal fixation system 21 against which the driving and attaching device 24 can engage to translate the translating member 22 as described in more detail below. It is noted that, in some procedures, the support rod 30 may be operatively positioned by bridging the support rod 30 over the vertebra to be reduced by attaching the support rod 30 to vertebra positioned on both sides of the vertebra to be reduced (as illustrated in FIG. 2, for example). Alternatively, other procedures may fix the support rod 30 in an operative position by it being cantilevered from an adjacent vertebra as may be accomplished by fixing the support rod 30 with one or more bone screws as implanted within one or more vertebrae. In any case, the support rod 30 provides a rigid structure from which to perform the reduction.

In some procedures, the medial/lateral connector 28 may be attached to the support rod 30 (such as by the set screws 52) before the translating member 22 is attached to the bone screw 32. In other procedures, the translating member 22 can be attached to the bone screw 32 to also be used as a guiding device for slidably guiding the medial/lateral connector 28 to the general location of the support rod 30. In such a procedure, the support rod 30 may be loosely fastened to an implanted portion of the spinal fixation system in order to allow for easy assembly and alignment of all components of the system, especially in a confined area. However, prior to performing reduction of the vertebra, the support rod 30 would preferably be rigidly secured to the implanted portion of the spinal fixation system (e.g. as a bridge or cantilever) and the medial/lateral connector 28 would be preferably rigidly attached to the support rod 30 (such as by set screw 52). This provides a stable and secure point from which driving of the translating member 22 can take place.

Figure 4:
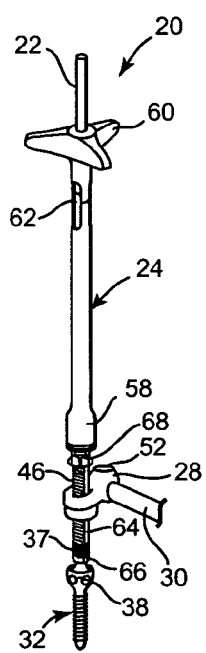
FIG. 4 is a perspective view of a surgical device in accordance with the present invention having a translating member attached to a bone screw to be implanted in a vertebra to be reduced.

Referring to FIG. 4, the translating member 22 is shown attached to the bone screw 32. That is, the threaded boss 44 of the translating member 22 is threaded into the tapped bore 40 of the bone screw 32 fully so as to time or provide a continuous threaded zone extending from threaded portion 46 of translating member 22 through the threaded portion 37 of stud 36. In this configuration, when the translating member 22 is attached to the bone screw 32, the translating member 22 passes through the opening 54 of the medial/lateral connector 28 and opening 73 of the seat portion 72. Referring back to FIG. 9, the flats 64 of the threaded portion 46 of the translating member 22 are rotationally limited by the width defining surfaces of slotted opening 54 of the medial/lateral connector 28. As such, the threaded portion 46 of the translating member 22 can translate linearly with respect to the medial/lateral connector 28. Likewise, referring to FIG. 8, the flats 66 of the threaded stud 36 of the bone screw 32 can also be positioned within the slotted opening 54 to limit rotation of the threaded stud 36 with respect to the medial/lateral connector 28 and to allow linear translation with respect to the medial/lateral connector 28. Preferably, when the translating member 22 is attached to the bone screw 32 and threaded portions 46 and 37 are timed together, the flats 64 of the translating member and the flats 66 of the bone screw align with one another. Such alignment allows the translating member 22 to pull the bone screw 32 into the opening 54 of the medial/lateral connector 28 so that the bone screw 32 can eventually be attached to the medial/lateral connector 28.

Figure 5:
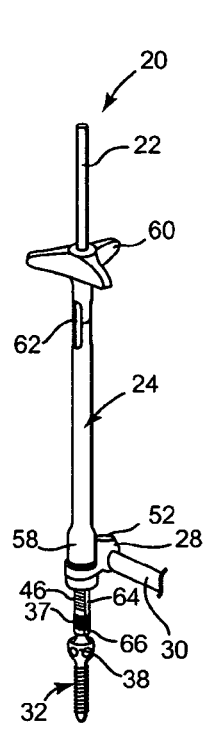
FIG. 5 is a perspective view of the surgical device of FIG. 4 wherein a driving and attaching device of the surgical device is engaged with the connector fixed with the support rod for translating the translating member and bone screw with respect to the connector.

Further referring to FIG. 4, a nut 68 is shown positioned near a proximal end 70 of the threaded portion 46 of the translating member 22. In this position, the nut 68 can be rotated to engage the threaded portion 46. The nut 68 can be threaded onto the threaded portion 46 in any desired manner. For example, the nut can be threaded onto the threaded portion 46 by hand. Preferably, however, the nut 68 is loaded into the socket 58 of the driving and attaching device 24 and retained by the capture device 63. The driving and attaching device 24 can then be coaxially positioned over the translating member 22. The driving and attaching device 24 can then be rotated by the handle 60 in order to thread the nut 68 onto the threaded portion 46 of the translating member 22. Continued rotation of the driving and attaching device 24 can be used to drive the nut 68 along the threaded portion 46 until the nut 68 engages with the medial/lateral connector 28 as illustrated in FIG. 5.

The driving and attaching device 24 can then be used to translate the translating member 22 in a reduction direction 26. With the medial/lateral connector 28 rigidly attached to a spinal fixation system, the medial/lateral connector 28 and the nut 68 can remain substantially stationary. As the nut 68 is further rotated relative to the non-rotational translating member 22, the translating member 22 is driven in the reduction direction 26 by the interaction between the threaded portion 46 of the translating member 22 and the nut 68. The flats 64 prevent rotation of the translating member 22 as the translating member 22 is linearly driven by the nut 68. It is noted that other anti-rotation or torque limiting devices may be used in place of or in addition to the flats described above. For example, a device could be used to control rotation of the translating member at a proximal end of the translating member such as a handle or the like.

Continued rotation of the handle 60 and thus the socket 58 of the driving and attaching device 24 thus draws the bone screw 32 closer to the medial/lateral connector 28 as shown in FIG. 6. As the threaded stud 36 of the bone screw 32 is drawn into the opening 54 of the medial/lateral connector 28, the flats 66 of the threaded stud 36 that are preferably aligned with flats 64 prevent rotation of the threaded stud 36 in the same way as threaded portion 46. As the threaded stud 36 further passes through the opening 54 of the medial/lateral connector 28, the nut 68 passes over the interface formed, by the timed threads that are aligned to create a continuous threading for the nut 68 to follow from the threaded portion 46 of the translating member 22 to the threaded portion 37 of the stud 36. As such, the driving and attaching device 24 can be used to both drive the bone screw 32 into an attachment position relative to the medial/lateral connector 28 and attach the nut 68 to the threaded stud 37 of the bone screw 32.

In FIG. 7, the bone screw 32 is shown in a seated position with respect to the medial/lateral connector 28. Referring back to FIGS. 8 and 10, the medial/lateral connector 28 preferably includes the seat surface 72 that can receive the corresponding ball shaped portion 74 of the bone screw 32. Once the bone screw 32 is seated with respect to the medial/lateral connector 28, it is preferable to lock the resultant construct by any conventional or developed technique for maintaining the nut 68 in position. For example, the nut 68 can be tightened to a desired torque or it can be locked in place by any other mechanism including torque-less devices. Alternatively, other components such as pins or adhesives can be used to hold the nut 68 or equivalent in place.

Seating the ball portion 74 to the seat surface 72 is preferable as a final securement of the bone screw 32 to the fixation system, such as by the force created by the nut 68. The distance of a reduction procedure would thus be determined by the degree of implant of the bone screw 32 in a vertebra and the functional fixed point provided by the spinal fixation system, which preferably comprises the support rod 30 as previously fixed in place to other vertebrae. The shape of the support rod 30, including any bends, could be present in order to achieve a desired reduction. As above, preferably such a reduction technique would be controlled from bi-lateral positions of the spine with the reduction degree defined by a pair of support rods. Although it is not necessary that the bone engaging element seat against or engage the medial/lateral connector 28 or other device, such is preferable to make a rigid construct. In the case of using a medial/lateral connector 28, after a reduction process, the medial/lateral connector 28 can be loosened with respect to the support rod so that it rotates around it and to position the seat of the connector against the ball of the bone engaging element. Then, the connector can be retightened in position with respect to the support rod. It is preferable that the construct be locked in place after a reduction process so that the vertebra are maintained in the desired positions. In accordance with this aspect of the present invention, a reduction could be performed and the bone screw 32 could be connected to the spinal fixation system by the use of the driving and attaching device 24. Any length of stud 36 length may be provided to facilitate this type of connection.

Also, in accordance with the present invention, the translating member 22 can be provided and driven in many different ways. That is, the translating member 22 is not limited to a threaded rod as illustrated. For example, a translating member can be any device or structural component capable of causing translation of a bone engaging member implanted in a vertebra and to which the translating member is attached such that the bone engaging element can be positioned in a desired position with respect to a spinal fixation system. For example, a translating member can comprise a chain, cable, rigid member, or combinations thereof. A translating member can be driven by any driving device or mechanism. For example, a driving device may provide a driving force to a translating member by using a device comprising a rack and pinion, frictional engagement, gears and chains, belts or wires and pulleys, and the like. If desired, a motorized driving device can be used.

Likewise, the driving and attaching device 24 can include any device or mechanism capable of attaching a bone engaging element to a spinal fixation system. That is, the invention is not limited to attaching bone engaging components to spinal fixation systems by threaded fasteners. Any attachment device, mechanism, or technique can be used. For example, a bone engaging element and spinal fixation system can be attached by clamping devices, press fits, cold welds, fusion welds, rivets, and the like. As such, a driving and attaching device can include devices for performing attachment by such techniques in accordance with the invention.

In FIGS. 12 through 16 another surgical device 76 in accordance with of the present invention and a method of using the device are illustrated with respect to a medial/lateral connector 28, a support rod 30, and a bone screw 32 in a similar manner as discussed above. Generally, the surgical device 76 includes a translating member 78 and a driving and attaching device 80. As shown in FIG. 15, for example, the driving and attaching device 80 preferably comprises a number of components including a nut driver 82 and translating member drive components collectively noted at 84. The nut driver 82 can be used to attach the nut 68 to the threaded stud 36 of the bone screw 32 as described below. Also, the translating member drive components 84 can be used to translate the translating member 78 along a reduction direction 26.

Figure 17:
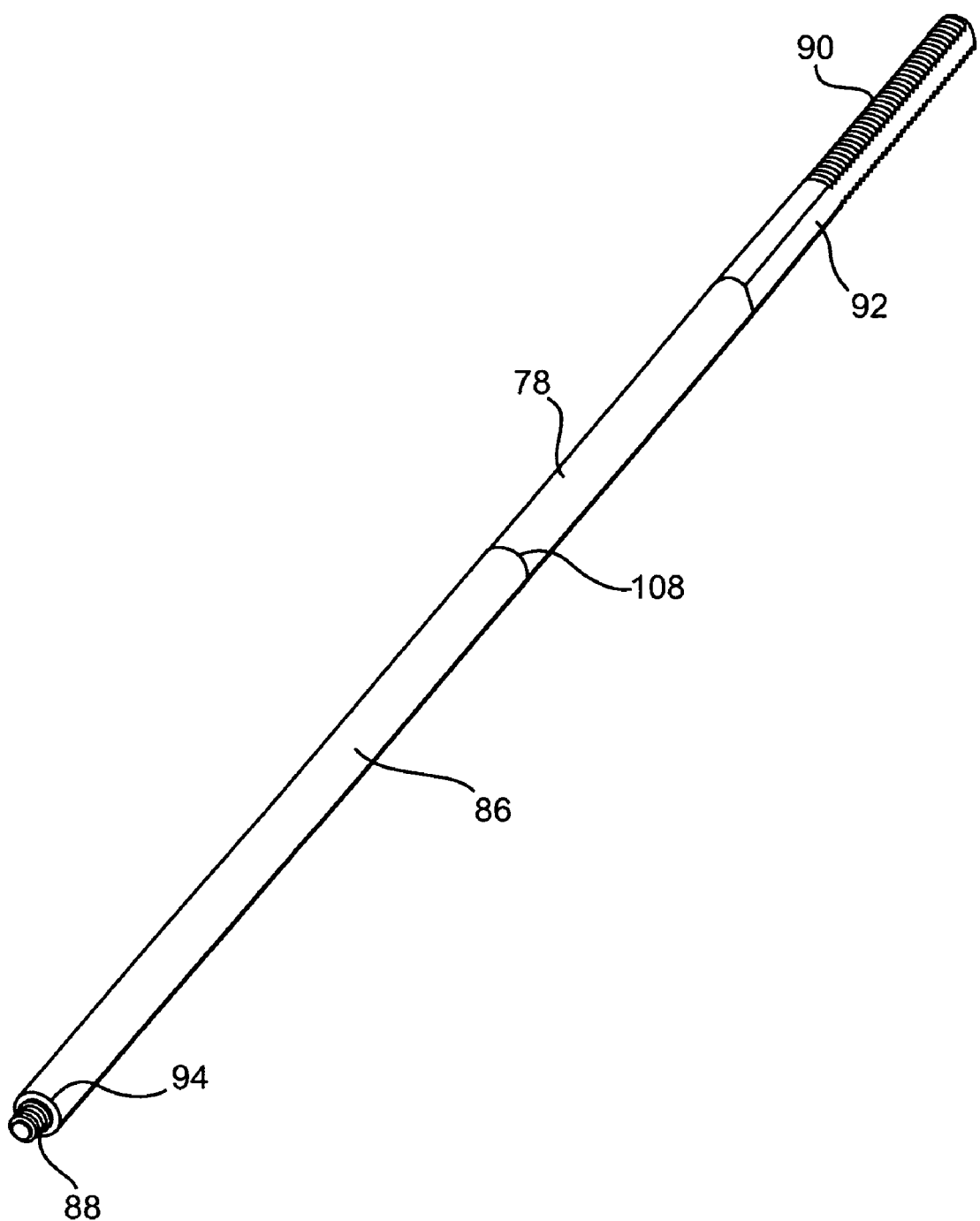
FIG. 17 is a perspective view of a translating member of the surgical device of FIGS. 13-16 showing a threaded portion spaced proximally from a distal end thereof and a threaded boss extending from the distal end thereof.

Referring to FIG. 17, the translating member 78 preferably comprises a linearly extending rod 86. Also, the translating member 78 preferably includes a threaded boss 88 extending from a distal end of the translating member 78. The threaded boss 88 can be used to attach the translating member 78 to the bone screw 32 by engaging with the tapped bore 40 of the stud 36. However, any attachment device as described or suggested above may be used. The translating member 78 also preferably comprises a threaded portion 90 that is spaced proximally from the distal end thereof. The threaded portion 90 is illustrated at the proximal end of the translating member 78, but need not be as will be apparent from the operation described below. The threaded portion 90 preferably includes flats 92 that can be aligned with the flats 66 of the threaded stud 37 of the bone screw 32 when the translating member 78 is attached to the bone screw 32. As shown, the translating member 78 includes a shoulder 94 around the boss 88 that can engage against a surface 96 at the end of the stud 36 of the bone screw 32 when the threaded boss 88 is threaded into the tapped bore 40. The threaded boss 88 can be rotationally timed so that the shoulder 94 engages with the surface 96 when the flats 92 of the translating member 78 are aligned with the flats 66 of the stud 36 of the bone screw 32.

As illustrated, the nut driver 82 can be similar to the driving device 24 described above. The nut driver 82 preferably includes a socket 98 at a distal end and a handle 100 spaced proximally for controllably rotating the socket 98. As shown, the driving and attaching device 80 also preferably includes a spacer 102 that can be integral with or made separately from the nut driver 82 and that can be used to space and functionally isolate the translating member drive components 84 from the nut driver 82.

With reference to FIG. 15, the translating member drive components 84 preferably include a driving nut 104 preferably shaped to facilitate its rotation and a handle 106. Preferably, the driving nut 104 and handle 106 are attached and rotatable with respect to each other; however, the driving nut 104 and the handle 106 may be provided as separate devices. The driving nut 104 preferably includes an internal threaded portion such as a tapped bore that can be used to thread the driving nut onto the threaded portion 90 of the translating member 78 as shown in FIG. 14. Also, the handle 106 preferably includes a passage 108 that is shaped and keyed to the flats 92 of the translating member 78 so that the handle 106 can prevent rotation of the translating member 78 while allowing the handle 106 to axially slide along the translating member 78. As such, the handle 106 can be used to prevent rotation of the translating member 78 when the translating member 78 is driven for a reduction by the driving nut 104 as described below.

In use, the surgical device 76 can be used to perform a reduction as described above. In an exemplary procedure, the translating member 78 can be attached to the bone screw 32 so that the translating member 78 passes through the opening 54 of the medial/lateral connector 28 as can be seen in FIG. 13. Next, the nut 68 and the nut driver 82 can be slid over and positioned coaxially with respect to the translating member 78. Preferably, the nut 68 is captured within the socket 98 of the nut driver 82 and the socket 98 is positioned adjacent to the medial/lateral connector 28 as illustrated in FIG. 14. In this position, the nut 68 is not engaged with the translating member 78 and both the nut driver 82 and nut 68 can freely move with respect to the translating member 78 including when the translating member is driven along a reduction direction 26.

After the nut driver 82 and the nut 68 are positioned over the translating member 78, the translating member drive components 84 can be positioned over and along the translating member 78. As shown in FIG. 14, the driving nut 104 can be rotated and thus threaded onto the threaded portion 90 of the translating member 78. As the driving nut 104 is threaded onto the translating member 78 the handle 106 can follow the driving nut 104 as it slides along the flats 92 of the translating member 78. The driving nut 104 can then be threaded down along the threaded portion 90 of the translating member 78 until the driving nut 104 engages with the spacer 102. At this point, further rotation of the driving nut 104 while preferably precluding rotation of the translating member 78 by holding handle 106 against rotation causes the translating member 78 to be driven along a reduction direction 26 thereby drawing the bone screw toward the medial/lateral connector 28.

Preferably, the handle 106 can be also used to orient the flats 66 of the threaded stud 36 of the bone screw 32 so that the flats 66 can be aligned with the sides of the slot 54 in the medial/lateral connector 28 during this procedure. The handle 106 can be rotated to rotate the translating member 78 about its longitudinal axis. Rotation of the translating member 78 will also rotate the stud 36, which preferably is rotatable to the ball portion 74 of the bone screw 32, relative to the bone screw 32 as implanted in a vertebra. The stud 36 of the illustrated bone screw 32 in FIG. 8 can be rotated independently from the course-threaded portion 34 by way of another ball and socket joint 75 as provided in a known manner to also permit articulation of the stud 36 so that the flats 66 can be aligned with the slot 54 of the medial/lateral connector 28. As shown, the passage 108 of the handle 106 is preferably configured so that when the handle 106 is in line with the support rod 30 the flats 66 will be aligned with the slot 54 so that the threaded stud 36 of the bone screw 32 can be drawn into the slot 54 of the medial/lateral connector 28.

The threaded stud 36 of the bone screw 32 is preferably drawn into and through the slot 54 of the medial/lateral connector 28 until the threads of the threaded stud 36 are positioned adjacent to the threads of the nut 68 as positioned within the socket 98 of the nut driver 82. That is, the threaded stud 36 becomes positioned so that the nut 68 can be started or threaded onto the threaded stud 36 by rotating the nut driver 82 with its handle 100.

The position of the threaded stud 36 with respect to the nut 68 can be monitored by using an indicator device. For example, as shown in FIG. 12, the translating member 78 includes a mark 109 that can be viewed through a window 110 of the nut driver 82. Also as shown the nut driver 82 can have a mark 112 that can be used together with the mark 109 of the translating member 78 to identify the position of the threaded stud 36 with respect to the nut 68. Preferably and as illustrated, the mark 109 lines up with the mark 112 when the threaded stud 36 is in a position where the nut 68 can be started by the nut driver 82 (in between the positions shown in FIGS. 15 and 16). At this point, further driving of the translating member 78 by the driver nut 104 is preferably stopped. Thereafter, the nut driver 82 is preferably used to thread the nut 68 on to the threaded stud 36, which action causes further translation of the translating member 78 in a similar manner as the previous embodiment of the driving and attaching device 24 with respect to the translating member 22. If the nut driver 82 is permitted to freely rotate around the translating member 78 effectively (i.e. where the action of threads 37 on nut 68 would rotate it and the nut driver 82), continued rotation of driver nut 104 could be done to cause further translation. Preferably, for any further translation of the bone screw 32, the nut driver 82 can be used to drive the nut 68 against the medial/lateral connector 28 for moving and eventually seating the bone screw 32 with respect to the medial/lateral connector 28 if desired and as described above. At this point the nut 68 can be torqued to specification as described above and the surgical device 76 can be disconnected from the bone screw 32 by unscrewing the translating member 78 from the stud 36 of the bone screw 32. As with the embodiment above, the reduction and subsequent disconnection can be done at any time once the nut 68 and threads 37 effectively engage to hold the support rod 30 or other fixation element to the bone engaging element.

Figure 18:
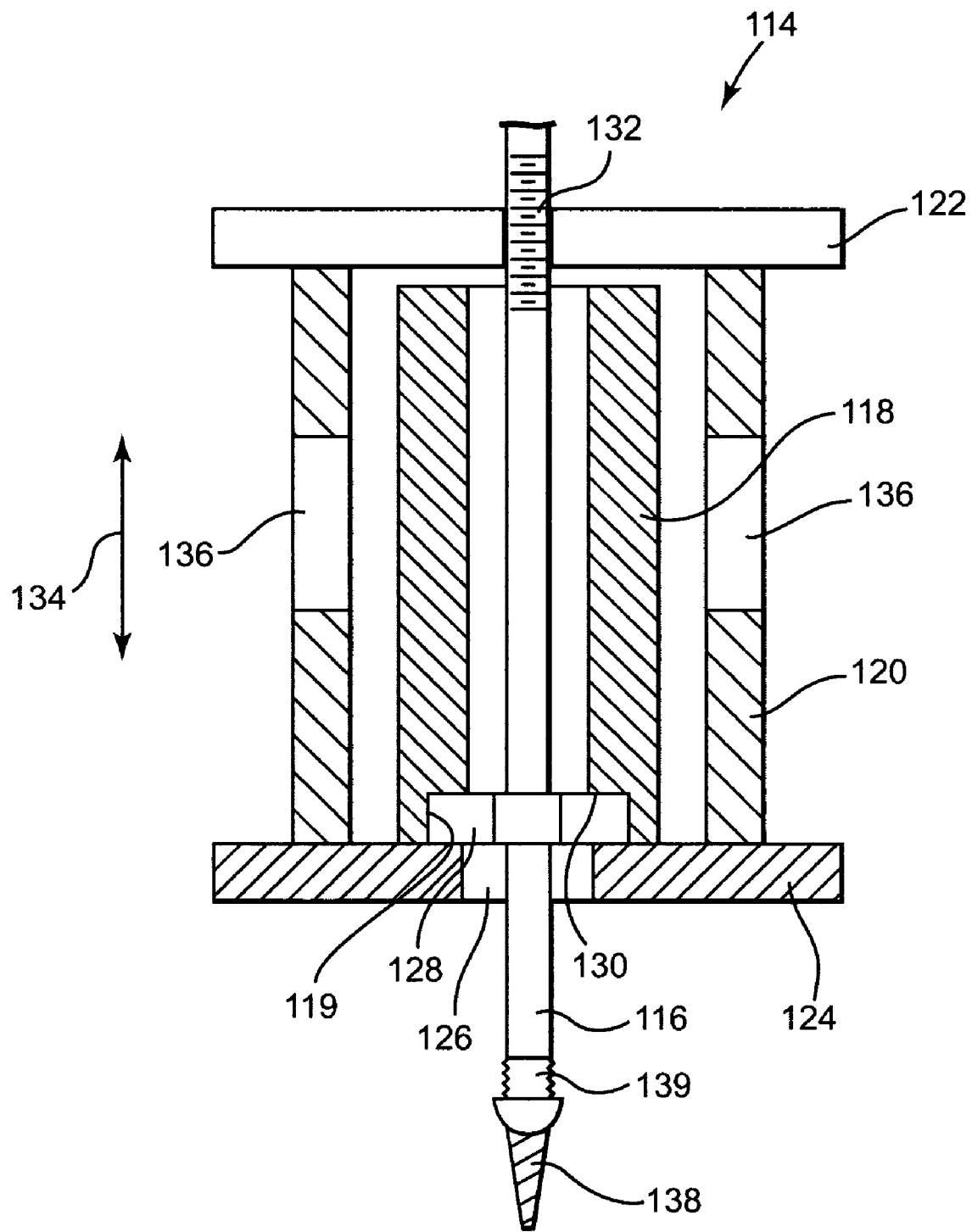
FIG. 18 is a schematic partial cross-sectional view of a surgical device in accordance with the present invention shown engaged with a connector of a spinal fixation system.

Referring to FIG. 18 another surgical device 114 that can be used to reduce a vertebra in accordance with the invention is schematically shown in partial cross-section. Generally, the surgical device 114 includes a translating member 116 connectable to bone screw 138, a nut driver 118 with a socket portion 119, a support tube 120, and a reduction nut 122. As shown, the device 114 is positioned adjacent to a connector 124 (such as like connector 28 above) and includes an opening 126 for receiving a threaded stud 139 of a bone screw 138 or the like that is shown connected with the translating member 116 and to eventually be connected to the connector 124 by a nut 128.

In use, the reduction nut 122 can be threaded onto an intermediate or proximal threaded portion 132 of the translating member 116 and can then be rotationally driven against the support tube 120 for driving the translating member 116 along a reduction axis 134. Preferably, the support tube 120 engages with the connector 124 such that the support tube 120 can be prevented from rotating. For example, the support tube 120 may be clamped to the connector 124 or may include mating features for mating with the connector 124. The translating member 116 can be held from rotation by a handle like handle 106 described above or the translating member 116 may include flats adjacent its distal end that are preferably aligned with flats of the stud 139 so that a slotted opening 126 of the connector 124 (as it is fixed in position) can prevent rotation of the translating member 116. Thus, like the embodiments described above, rotation of reduction nut 122 can cause controlled translation.

The reduction nut 122 can then be used to drive the translating member 116 so that a threaded stud 139 of a bone screw 138 or the like can be positioned within the opening 126 of the connector 124 as described above. When the threaded stud 139 of the bone screw 138 is positioned adjacent to the nut 128, the nut driver 118 can be rotated to thread the nut 128 onto the threaded stud 139 and continue translation of translating member 116. Further rotation of the nut driver 118 can be done until the reduction is complete, such as when the connector 124 and bone screw 138 seat together. In order to provide access to rotate the nut driver 118, the support tube 120 can include openings 136 that provide such access for rotating the nut driver 118 and nut 128. Nut driver 118 can be shaped or provided with any surface feature to facilitate its rotation by way of access through the support tube 120.

The present invention has now been described with reference to certain specific embodiments. The foregoing detailed description has been given for clarity of understanding. Others may recognize that changes can be made in the described embodiments without departing from the scope and spirit of the invention. Thus, the scope of the present invention should not be limited to the exact details and structures described herein.

What is claimed is:

1. A multifunction surgical device for positioning a bone engaging element with respect to a component of a spinal fixation system and for attaching the bone engaging element to the component of the spinal fixation system, the surgical device comprising:

a translating member having a reduction axis and having an attachment device at a distal end capable of engaging a bone engaging element implanted in a vertebra;

a driving and attaching device coaxial with the translating member; and capable of non-rotationally axially driving the translating member along the reduction axis for translating a bone engaging element removably engaged with the attachment device of the translating member and implanted in a vertebra to an attachment position with respect to a component of a spinal fixation system while engaging a component of the spinal fixation system with a portion of the driving and attaching device, the driving and attaching device capable of attaching a fastener to the bone engaging element removably engaged with the translating member;

wherein the translating member comprises a threaded portion at the distal end thereof; and wherein the threaded portion of the translating member comprises a timed thread that can be positively rotationally aligned with a threaded portion of the bone engaging element wherein a threaded fastener can be uninterruptedly driven from the threaded portion of the translating member to the threaded portion of the bone engaging element.

2. A multifunction surgical device for positioning a bone engaging element with respect to a component of a spinal fixation system and for attaching the bone engaging element to the component of the spinal fixation system while engaging the surgical device with the spinal fixation system, the surgical device comprising:

a translating member having a reduction axis and having an attachment device at a distal end capable of detachably engaging a bone engaging element implanted in a vertebra, the attachment device comprising a threaded boss capable of engaging a tapped portion of the bone engaging element; and a fastener driving device configured to non-rotationally axially drive the translating member along the reduction axis for translating a bone engaging element removably engaged with the attachment device of the translation member and implanted in a vertebra to an attachment position with respect to a component of a spinal fixation system, the fastener driving device including a fastener driving portion configured to attach a fastener to a bone engaging element removably engaged with the translating member;

wherein the translating member comprises a threaded portion at the distal end thereof for driving the translating member along the reduction axis; and wherein the threaded portion of the translating member comprises a timed thread that can be positively rotationally aligned with a threaded portion of a bone engaging element wherein a threaded fastener can be uninterruptedly driven from the threaded portion of the translating member to the threaded portion of the bone engaging element.

3. A multifunction surgical device for positioning a bone engaging element with respect to a component of an orthopedic implant system and for attaching the bone engaging element to the component of the orthopedic implant system while engaging the surgical device with the orthopedic implant system, the surgical device comprising:

a translating member having a reduction axis and having an attachment device at a distal end capable of detachably engaging a bone engaging element implanted in a bone, the translating member further including a threaded portion at the distal end comprising a timed thread that can be positively rotationally aligned with a threaded portion of the bone engaging element;

means for non-rotationally axially driving the translating member along the reduction axis for translating a bone engaging element removably engaged with the attachment device of the translation member and implanted in a bone to an attachment position with respect to a component of an orthopedic implant system; and means for uninterruptedly driving a threaded fastener from the threaded portion of the translating member to the threaded portion of the bone engaging element to attach the threaded fastener to the bone engaging element.

4. The surgical device of claim 3, wherein the means for non-rotationally axially driving the translating member comprises a fastener driving device capable of driving a fastener along a threaded portion of the translating member while engaging the fastener with a component of an orthopedic implant system thereby driving the translating member along the reduction axis.

5. The surgical device of claim 3, wherein the means for attaching a fastener to a bone engaging element comprises a fastener driving device capable of driving a fastener along a threaded portion of the bone engaging element.

6. The surgical device of claim 3, wherein the means for non-rotationally axially driving the translating member and wherein the means for attaching a fastener to a bone engaging element comprises a driving device capable of driving a fastener along a threaded portion of the translating member while engaging the fastener with a component of an orthopedic implant system thereby driving the translating member along the reduction axis.

7. A method for positioning a bone engaging element implanted in a vertebra with respect to a component of a spinal fixation system and for attaching the bone engaging element to the component of the spinal fixation system, the method comprising the steps of:

engaging a component of a spinal fixation system with a multifunction surgical device comprising a translating member having a reduction axis and a driving and attaching device capable of driving the translating member along the reduction axis and for attaching a fastener to the bone engaging element;

removably attaching the translating member of the multifunction surgical device to a previously implanted bone engaging element implanted in a vertebra;

driving the bone engaging element with respect to the component of the spinal fixation system by driving the translating member along the reduction axis with the driving and attaching device of the multifunction surgical device;

rotatably attaching a fastener to the bone engaging element with the driving and attaching device of the multifunction surgical device; and detaching the translating member of the multifunction surgical device from the bone engaging element;

wherein the step of attaching a fastener to the bone engaging element comprises uninterruptedly driving a fastener from a threaded portion of the translating member to a threaded portion of a bone engaging component.

8. The method of claim 7, wherein the step of attaching the translating member of the multifunction surgical device comprises engaging a threaded portion of the translating member with a threaded portion of a bone engaging element.

9. The method of claim 7, wherein the step of driving the bone engaging element with respect to the component of the spinal fixation system comprises positioning the bone engaging element in an attachment position with respect to the component of the spinal fixation system.

10. The method of claim 7, wherein the step of driving the bone engaging element with respect to the component of the spinal fixation system comprises preventing rotation of the translation member with respect to the reduction axis of the translation member while driving the translation member along the reduction axis.

11. The method of claim 7, wherein the step of driving the bone engaging element with respect to the component of the spinal fixation system comprises driving the translation member by engaging the driving and attaching device with a threaded portion at a distal end of the translating member.

12. The method of claim 11, wherein the step of driving the translating member by engaging the driving and attaching device with a threaded portion at a distal end of the translating member comprises engaging a fastener with the threaded portion and driving the fastener with the driving and attaching device.

13. The method of claim 12, wherein the step of driving the translation member by engaging the driving and attaching device with a fastener comprises driving the fastener against a component of a spinal fixation system.

14. The method of claim 7, wherein the step of driving the bone engaging element with respect to the component of the spinal fixation system comprises driving the translation member by engaging the driving and attaching device with a threaded portion spaced apart from the distal end of the translating member.

15. The method of claim 7, further comprising the step of detaching the translating member of the multifunction surgical device from the bone engaging element.

16. An anchoring device for use with a spinal fixation system, the spinal fixation system including at least one spine stabilizing rod and at least one connector for attaching the spine stabilizing rod to the anchoring device, the anchoring device comprising:

a bone engaging portion at a distal end thereof; and a reduction and attachment device extending from the bone engaging portion and comprising first and second threaded portions extending along a reduction axis, the first threaded portion spaced apart from the bone engaging portion, the second threaded portion detachably engaged with the first threaded portion and rotationally aligned with the first threaded portion such that the threads of the second threaded portion align with and uninterruptedly continue the threads of the first threaded portion, the reduction and attachment device capable of being positioned relative to a connector of a spinal fixation system such that a fastener can be driven along the second threaded portion and against the connector for translating the bone engaging portion along the reduction axis and uninterruptedly pass from the second threaded portion to the first threaded portion for attaching the anchoring device to the connector.

* * * * *

UNITED STATES PATENT AND TRADEMARK OFFICE
CERTIFICATE OF CORRECTION

PATENT NO.       : 7,591,836 B2                              Page 1 of 1
APPLICATION NO.  : 10/903910
DATED            : September 22, 2009
INVENTOR(S)      : Dick et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1323 days.

Signed and Sealed this

Twenty-first Day of September, 2010

David J. Kappos
*Director of the United States Patent and Trademark Office*